United States Patent [19]

Hannant

[11] Patent Number: 5,443,462

[45] Date of Patent: Aug. 22, 1995

[54] ELECTRICAL APPARATUS FOR CONTROLLING THE SUPPLY OF POWER TO AN INSERTABLE ELECTRODE

[75] Inventor: Keith Hannant, Rustington, England

[73] Assignee: Smiths Industries Public Limited Company, London, England

[21] Appl. No.: 45,178

[22] Filed: Apr. 13, 1993

[30] Foreign Application Priority Data

May 7, 1992 [GB] United Kingdom ............... 9209859

[51] Int. Cl.6 .............................................. A61B 17/39
[52] U.S. Cl. ......................................... 606/34; 606/41; 606/42
[58] Field of Search .................. 606/32, 34–35, 606/37–42, 45, 49; 219/240

[56] References Cited

U.S. PATENT DOCUMENTS

| 3,089,496 | 5/1963 | Degelman | 606/39 X |
|---|---|---|---|
| 3,933,157 | 1/1976 | Bjurwill et al. | 606/35 |
| 4,096,545 | 6/1978 | Helwig | 361/380 |
| 4,463,759 | 8/1984 | Garito et al. | 128/303.14 |
| 4,812,623 | 3/1989 | Haden | 219/437 |
| 4,936,842 | 6/1990 | D'Amelio et al. | 606/42 |
| 5,067,953 | 11/1991 | Feucht | 606/42 |

FOREIGN PATENT DOCUMENTS

| 1146989 | 4/1963 | Germany | 606/35 |
|---|---|---|---|
| 2803275 | 8/1979 | Germany | 606/42 |
| 1333573 | 10/1973 | United Kingdom . | |
| 1498338 | 1/1978 | United Kingdom . | |

*Primary Examiner*—Lee S. Cohen
*Attorney, Agent, or Firm*—Pollock, VandeSande and Priddy

[57] ABSTRACT

The handset of electrosurgery or welding apparatus has two spaced contacts which make connection with the shaft of an electrode that is insertable into the handset. A low power alternating signal generator is connected to the forward contact. When the electrode is fully inserted into the handset and contacts the rear contact, the alternating signal is supplied to a detector. The detector is connected to a power generator and rams it on when the alternating signal is detected so that electrosurgery power is supplied to the forward contact.

10 Claims, 1 Drawing Sheet

ELECTRICAL APPARATUS FOR CONTROLLING THE SUPPLY OF POWER TO AN INSERTABLE ELECTRODE

BACKGROUND OF THE INVENTION

This invention relates to electrical apparatus.

The invention is more particularly concerned with apparatus having an electrode mounted in a handset and supplied with electrical power. The apparatus might, for example, be electrosurgery apparatus or welding apparatus.

In electrosurgery apparatus, the handset has an electrically-insulating casing that may have one or more switches to control supply of power to the electrode. The metal electrode itself is a sterilizable component that is plugged into a socket in the handset. Different shape electrodes can be used for different applications, with the same handset. RF power is supplied from the supply unit, via a cable, to the socket in the handset and thereby to the electrode.

One problem that arises is that, if the electrode were not fully inserted in the handset, it might not make proper electrical contact with the socket. This could cause arcing within the handset between the socket and the electrode and a reduction in the power supplied to the electrode that may not be immediately apparent to the user. The arcing could also lead to damage to the electrode or to the handset.

SUMMARY OF THE INVENTION

It is an object of the present invention to provide electrical apparatus that avoids this problem.

According to the present invention there is provided electrical apparatus including a power supply unit, a handset having a contact adapted to make electrical connection with an electrode, a cable connecting the power supply unit to the contact in the handset, the handset being arranged to prevent supply of power to the contact unless the electrode is fully coupled with the handset.

The handset preferably includes a second contact arranged to be contacted by the electrode after the electrode is fully coupled with the first contact, the apparatus including switching means that controls supply of power to the cable such that power is supplied to the handset only when the second contact is contacted by the electrode. The supply unit may include a low power alternating signal generator arranged to supply an alternating signal to one of the first and second contacts, and detector means connected to the other of the first and second contacts, the detector means being responsive to the alternating signal at the other contact when the electrode is fully coupled with the handset so as to enable supply of power to the handset. The handset may include user-actuable switch means by which power supply to the electrode is controlled, the user-actuable switch means being disabled until the electrode is fully coupled to the handset. The handset may include two user-actuable switch means, the switch means being operable to connect the other of the contacts with respective lines connected to the detector means. One of the lines preferably includes a unidirectional current device, the detector means being responsive to rectified signals on the one line or unrectified signals on the other line to determine which of the two switches means is actuated. The handset may be an electrosurgery handset and the apparatus may include a large area return electrode.

Electrosurgery apparatus according to the present invention, will now be described, by way of example, with reference to the accompanying drawing.

DETAILED DESCRIPTION OF THE PREFERRED EMBODIMENTS

Figure 1:
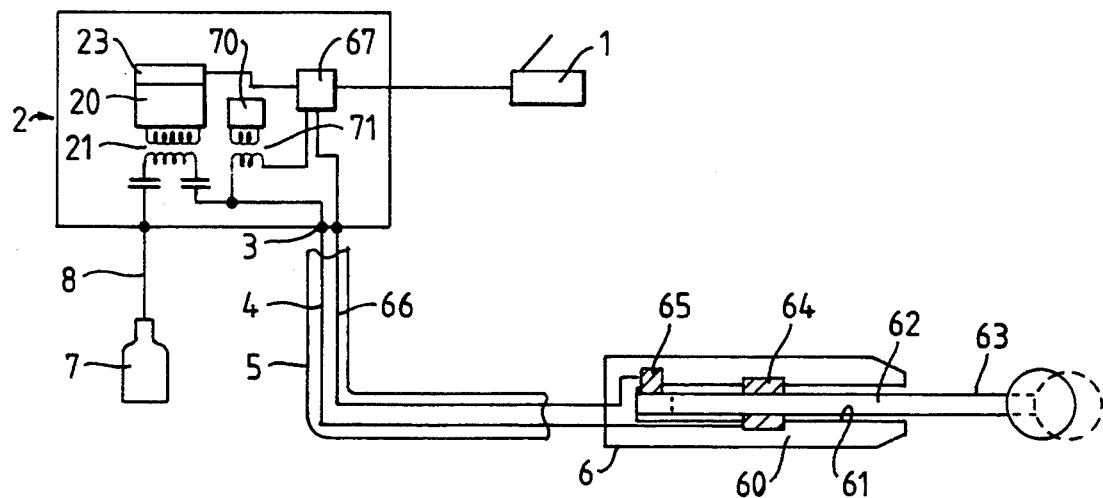
FIG. 1 is a partly schematic diagram of one form of the apparatus.

With reference to first to FIG. 1, there is shown electrosurgery apparatus in which power supply is controlled by a footswitch 1. The apparatus has a supply unit 2 with a power generator 20 that provides RF electrosurgery power at 500KHz via an output transformer 21 to an output 3. The output 3 is connected via a wire 4 in a cable 5 to a handset 6. Return power from the patient is taken from a return plate 7 via return cable 8 back to the supply unit 2.

The handset 6 has an electrically-insulative plastics housing 60 with a barrel 61 that is open at its forward end to receive the rear end or shank 62 of a metal electrode 63. The barrel 1 is closed at its rear end. Inside the barrel 61 there is a resilient metal collect or contact 64 the internal diameter of which is such that it makes a close sliding fit, and a good electrical contact, with the shank 62 of the electrode. The collet 64 is connected to the wire 4 in the cable 5 so that power can be supplied to the electrode 63 when it is coupled in the handset 6. At the rear end of the barrel 61, rearwardly of the collet 64, there is a second electrical contact 65 that is shaped and located so that it contacts the shank 62 of the electrode 63 only after it has passed the collet 64. The contact 65 is connected to a wire 66 that is preferably provided by a second core of the cable 5.

The supply unit 2 includes a low power alternating signal generator 70 (that is, with a power level below that capable of producing an electrosurgery effect) which supplies a 40KHz signal via an isolating transformer 71 to the power supply wire 4 and to a detector unit 67. The other wire 66 in the cable 5 is connected directly to the detector unit 67. This in turn is connected to a switch 23 that controls operation of the power generator 20. The detector unit 67 also receives on input from the footswitch 1. When the detector unit 67 detects the 40KHz signal and the footswitch 1 is on, the detector unit closes the switch 23 so that the power supply 20 is turned on. When no 40KHz signal is detected, or when the footswitch is off, the detector unit 67 holds the switch 23 open so that the power supply 20 is turned off.

In normal, correct use, the shank 62 of the electrode 63 is fully inserted into barrel 61 so that it abuts the closed rear end of the barrel. In this position, the collet 64 makes electrical connection with the electrode 63 at a point forwardly of its rear end. The rear end of the electrode 63 makes contact with the second or rear contact 65 so that the two contacts 64 and 65, and hence the two wires 4 and 66, are bridged by the shank 62 of the electrode. Thus, when the surgeon depresses the footswitch 1, the detector unit 67 turns on the switch 23 causing the generator 20 to supply power to the transformer 21 and hence to the electrode 63.

If, however, the electrode 63 were not fully inserted, and were located, for example, in the position shown by the broken lines in FIG. 1, the shank 62 would not make contact with the contact 65. In this position, therefore, the detector unit 67 would maintain the switch 23 off, preventing supply of power to the handset 6. Because power is not supplied to the handset 6 when the electrode 63 is not fully inserted, there is no risk of arcing in the handset between the electrode and the handset contact 64.

Various modifications are possible. For example, it is not essential to sense full insertion of the electrode in the way described. Instead, for example, the handset could include an electrical switch with a mechanical contact that is displaced on full insertion of the electrode, so that the switch is closed and power is then supplied to the electrode contact.

Figure 2:
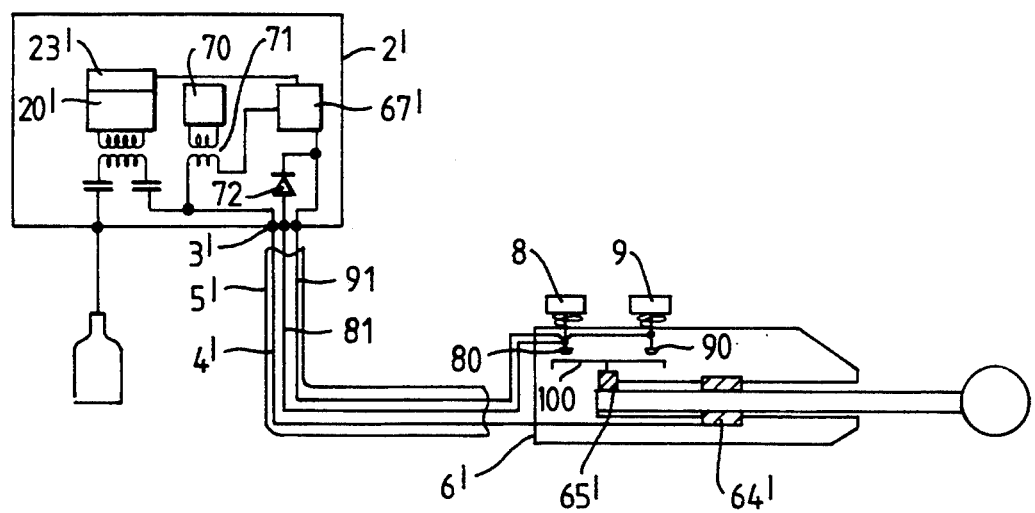
FIG. 2 is a partly schematic diagram of an alternative form of apparatus.

Alternative apparatus is shown in FIG. 2 in which the footswitch shown in the arrangement of FIG. 1 is replaced by switches in the handset 6' itself.

The handset 6' is similar to that in FIG. 1 except that it has two push-button switches 8 and 9 one of which is held down by the surgeon when he wishes to apply a cutting RF waveform or a coagulation waveform respectively. The cut switch 8 has a spring contact 80 that is connected via a wire 81 to the supply unit 2'; the coagulate switch 9 has a similar contact 90 that is connected via a wire 91 to the supply unit. Located beneath the two spring contacts 80 and 90 is a metal plate 100 that extends to a contact 65' of the same kind and located in the same position as the contact 65 shown in FIG. 1. In their natural, rest position, both spring contacts 80 and 90 are spaced above the plate 100 so that there is no electrical connection between the contact 65' and either of the wires 81 and 91. If, however, the cut button 8 were depressed, this would push contact 80 against the plate 100 and establish contact between wires 81 and the power supply wire 4'.

The supply unit 2' includes a low power signal generator 70 that supplies a 40KHz signal via an isolating transformer 71 to the power supply line 4' and to a detector unit 67'. One of the wires 91 in the cable 5' is connected directly to the detector unit 67' whereas the other wire is connected to the detector via a diode 72 or other unidirectional current device. When the cut button 8 is depressed and contact is established between wires 81 and 4', the 40KHz signal on the power supply line 4' will be supplied via the diode 72 to the detector unit 67'. The signal received by the detector unit 67' is, therefore, a rectified half-wave signal that the detector unit identifies as a cut command. In response to this, the detector unit 67' signals the switch 23' in the power generator 20' to cause the generator to supply a cut waveform signal to the output.

Similarly, when the coagulate button 9 is depressed, the 40KHz signal on the power wire 4' is supplied via wire 91 directly to the detector unit 67' in an unrectified form. The detector unit 67' identifies this unrectified signal as a coagulate command and, accordingly, signals the switch 23' to switch the generator 20' to a coagulate waveform output.

As in the arrangement of FIG. 1, if the electrode 6Y were not fully coupled with the handset 6' it would not make connection with the rear cornact 65' and the detector unit 67' would receive no signal from the signal generator 70. The detector unit 67' would then maintain the switch 23' open so that no power was supplied by the generator 20' to the output and hence to the power supply contact or collet 64' in the handset.

It will be appreciated that the invention could be used in other electrical apparatus having an electrode mounted in a handset to which electrical power is supplied. One example of such apparatus is electrical arc welding apparatus.

What I claim is:

1. Electrosurgery apparatus comprising: a power supply unit; an electrode; a handset having a barrel with a forward end and a rear end, said forward end of the barrel being open and receiving a rear end of said electrode inserted therein; a first contact mounted in said barrel of said handset at a location forwardly of the rear end of the barrel; insertion detection means located in the barrel rearwardly of said first contact for detecting insertion of said rear end of the electrode rearwardly of said first contact; a cable connecting said power supply unit to said first contact in the handset; and switch means that is actuable by a user to cause said power supply unit to supply power to said electrode only if the electrode is inserted correctly into said handset as far as said insertion detection means.

2. Electrosurgery apparatus according to claim 1, wherein the insertion detection means includes a second contact that is arranged to be contacted by the electrode after the electrode is fully coupled with the first contact.

3. Electrosurgery apparatus according to claim 2, wherein the power supply unit includes a low power alternating signal generator supplying an alternating signal to one of the first and second contacts, and a detector unit connected to the other of the first and second contacts, said detector unit being responsive to the alternating signal at said other contact when the electrode is fully coupled with the handset so as to enable supply of power to the handset.

4. Electrosurgery apparatus according to claim 3, wherein said switch means includes two user-actuable switches mounted on said handset, said cable including two lines connected to the insertion detection means, said switches being operable to connect said other contact with respective ones of said lines.

5. Electrosurgery apparatus according to claim 4, wherein the apparatus includes a unidirectional current device connected in series with one of the lines, and wherein the detector unit is responsive to rectified signals on said one line or unrectified signals on the other line to determine which of the two switches is actuated.

6. Electrosurgery apparatus according to claim 1, wherein said switch means is mounted on said handset.

7. Electrosurgery apparatus according to claim 1, wherein the apparatus includes a large area return electrode connected with the power supply unit.

8. Electrosurgery apparatus comprising: a power supply unit; a return electrode; a first second cable connecting the return electrode with the power supply unit; an active electrode; a handset having a barrel with a forward end and a rear end, said forward end of the barrel being open and receiving a rear end of said active electrode inserted therein; a first contact mounted in the barrel at a location forwardly of said rear end of the barrel; a second contact located in the barrel rearwardly of said first contact for electrical contact with the rear end of the active electrode rearwardly of said first contact after the electrode is fully in contact with the first contact; a second cable connecting said power supply unit with said first and second contacts in the handset; a low power alternating signal generator and a detector unit in the power supply unit, and wherein the second cable connects said low power generator to one of the first and second contacts and connects the other of the first and second contacts to said detector unit such that the detector unit only enables supply of electrosurgery power to the first contact when it detects an alternating signal from the low power signal generator via the cable indicative of correct connection of the active electrode in the handset.

9. Electrosurgery apparatus according to claim 8, wherein the handset includes two user-actuable switches, wherein the second cable includes two lines connected to said detector unit, and wherein the switches are operable to connect said other contact with respective ones of the lines.

10. Electrosurgery apparatus according to claim 9, wherein the apparatus includes a unidirectional current device connected in series with one of the lines, and wherein said detector unit is responsive to rectified signals on one of the lines or unrectified signals on the other of the lines to determine which of the two switches is actuated.

* * * * *